US010345240B2

(12) United States Patent
Chan et al.

(10) Patent No.: US 10,345,240 B2
(45) Date of Patent: Jul. 9, 2019

(54) WIRELESS COMMUNICATION DEVICE-BASED DETECTION SYSTEM

(71) Applicant: The Governing Council of the University of Toronto, Toronto (CA)

(72) Inventors: Warren Che Wor Chan, Toronto (CA); Kevin Ming, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 14/651,538

(22) PCT Filed: Dec. 11, 2013

(86) PCT No.: PCT/CA2013/050953
§ 371 (c)(1),
(2) Date: Jun. 11, 2015

(87) PCT Pub. No.: WO2014/089700
PCT Pub. Date: Jun. 19, 2014

(65) Prior Publication Data
US 2015/0323461 A1 Nov. 12, 2015

Related U.S. Application Data

(60) Provisional application No. 61/735,847, filed on Dec. 11, 2012.

(51) Int. Cl.
*G01N 21/64* (2006.01)
*G01N 21/25* (2006.01)
*G01J 3/02* (2006.01)
*G01J 3/44* (2006.01)
*G01N 33/58* (2006.01)
(Continued)

(52) U.S. Cl.
CPC ........ *G01N 21/6458* (2013.01); *G01J 3/0272* (2013.01); *G01N 21/25* (2013.01); *G01N 21/6428* (2013.01); *G01N 21/6456* (2013.01); *G01N 33/536* (2013.01); *G01N 33/54373* (2013.01); *G01N 33/588* (2013.01); *H04M 1/72569* (2013.01); *G01N 35/00871* (2013.01); *G01N 2201/0221* (2013.01);
(Continued)

(58) Field of Classification Search
None
See application file for complete search history.

(56) References Cited

U.S. PATENT DOCUMENTS

| 2007/0166835 A1* | 7/2007 | Bobrow | C12Q 1/6834 436/174 |
| 2012/0288849 A1* | 11/2012 | Won | G06F 19/24 435/5 |
| 2014/0193839 A1* | 7/2014 | Cunningham | G01J 3/28 435/7.92 |

OTHER PUBLICATIONS

Yager, P. et al. (2006) Microfluidic diagnostic technologies for global public health. Nature 442:412-8.
(Continued)

*Primary Examiner* — Neil N Turk
(74) *Attorney, Agent, or Firm* — Eduardo Krupnik

(57) ABSTRACT

The invention combines recent advances in barcode technology with portable wireless communication devices to engineer a simple and low-cost chip-based multiplex wireless detection system. The system can analyze multiple targets of interest simultaneously in minutes and is applicable to detection of pathogens or contaminants in a wide range of fields including medicine, agriculture and the environment.

20 Claims, 9 Drawing Sheets

Specification includes a Sequence Listing.

(51) Int. Cl.
H04M 1/725 (2006.01)
G01N 33/543 (2006.01)
G01N 33/536 (2006.01)
G01N 35/00 (2006.01)

(52) U.S. Cl.
CPC ... G01N 2201/061 (2013.01); G01N 2201/12 (2013.01); H04M 1/72527 (2013.01)

(56) References Cited

OTHER PUBLICATIONS

Chin, C.D., et al. (2007) Lab-on-a-chip devices for global health: past studies and future opportunities. Lab on a chip 7:41-57.
Martinez, A.W., et al. (2010) Diagnostics for the developing world: microfluidic paper-based analytical devices. Anal. Chem. 82:3-10.
Mudanyali, O., et al. (2012) Integrated rapid-diagnostic-test reader platform on a cellphone. Lab Chip 12(15):2678-86.
Zhu, H., et al. (2012) Quantum dot enabled detection of *Escherichia coli* using a cell-phone. Analyst 137:2541-4.
Breslauer, D.N., et al. (2009) Mobile phone based clinical microscopy for global health applications. PloS One 4(7): e6320.
Korteweg, C. and Gu, J. (2010) Pandemic influenza A (H1N1) virus infection and avian influenza A (H5N1) virus infection: a comparative analysis. Biochem. Cell Biol. 88:575-87.
Smith, G.J.D., et al. (2009) Dating the emergence of pandemic influenza viruses. Proceedings of the National Academy of Sciences of the United States of America 106:11709-12.
Yerly, S., et al. (2001) Nosocomial outbreak of multiple bloodborne viral infections. The Journal of Infectious Diseases 184:369-72.
Chu, C., et al. (2001) Hepatitis C : Comparison with acute heptitis B-Comparison of clinical, virologic and pathologic features in patients with acute hepatitis B and C. Journal of Gastroenterology and Hepatology 16:209-214.
Giri, S., et al. (2011) Rapid screening of genetic biomarkers of infectious agents using quantum dot barcodes. ACS Nano 5:1580-7.
Klostranec, J.M., et al. (2007) Convergence of quantum dot barcodes with microfluidics and signal processing for multiplexed high-throughput infectious disease diagnostics. Nano Letters 7:2812-8.
Han, M., et al. (2001) Quantum-dot-tagged microbeads for multiplexed optical coding of biomolecules. Nature Biotechnology 19:631-5.
Walt, D.R. (2010) Fibre optic microarrays. Chemical Society Reviews 39:38-50.
Zhu, H., et al. (2011) Optofluidic fluorescent imaging cytometry on a cell phone. Analytical chemistry 83:6641-7.
Fournier-Bidoz, S., et al. (2008) Facile and rapid one-step mass preparation of quantum-dot barcodes. Angewandte Chemie 47:5577-81.
Peng, X., et al. (1997) Epitaxial Growth of Highly Luminescent CdSelCdS CorelShell Nanocrystals with Photostability and Electronic Accessibility. Journal of American Chemical Society 119:7019-7029.
Hines, M.A. and Guyot-Sionnest, P. (1996) Synthesis and Characterization of Strongly Luminescing ZnS-Capped CdSe Nanocrystals. Journal of Physical Chemistry 100:468-471.
Dabbousi, B.O., et al. (1997) (CdSe) ZnS Core-Shell Quantum Dots: Synthesis and Characterization of a Size Series of Highly Luminescent Nanocrystallites. Journal of Physical Chemistry B 101:9463-9475.
Guizar-Sicairos, M., et al. (2008) Efficient subpixel image registration algorithms. Optics Letters 33:156-8.
Guizar, M. (2008) Efficient subpixel image registration by cross-correlation. Available at http://www.mathworks.com/matlabcentral/fileexchange/18401-efficient-subpixel-image-registration-by-cross-correlation.
Ballard, D.H. (1981) Generalizing the Hough Transform to detect arbitrary shapes. Pattern Recognition 13:111-122.
Peng, T. (2010) Detect circles with various radii in grayscale image via Hough Transform. Available at http://www.mathworks.com/matlabcentral/fileexchange/9168-detect-circles-with-various-radii-in-grayscale-image-via-hough-transform.

\* cited by examiner

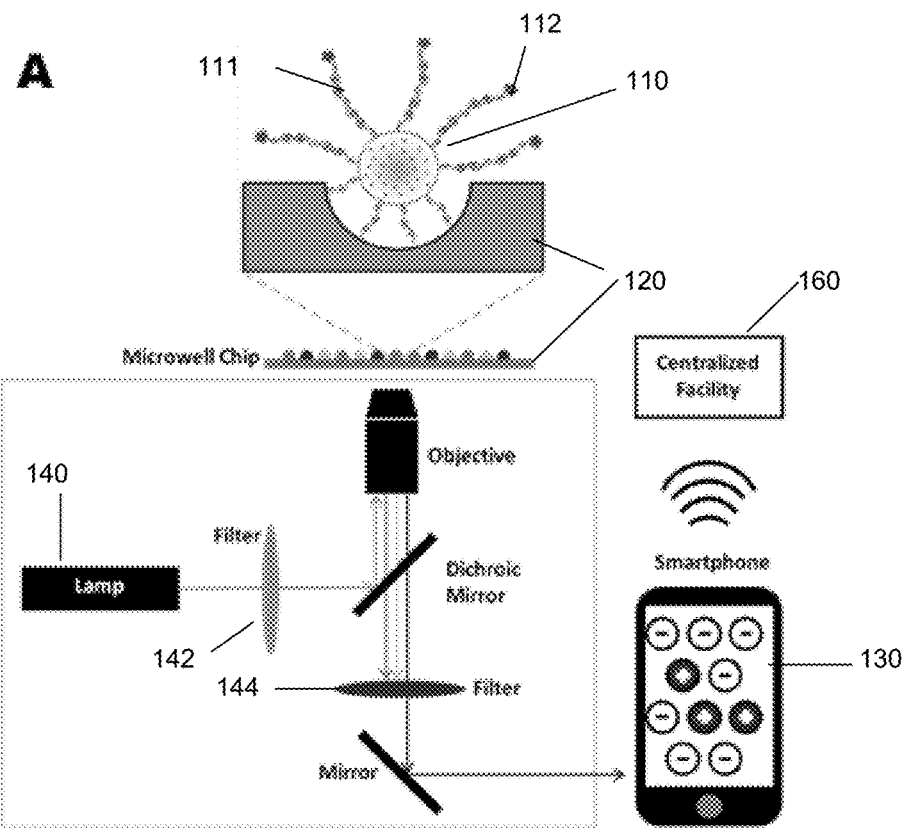
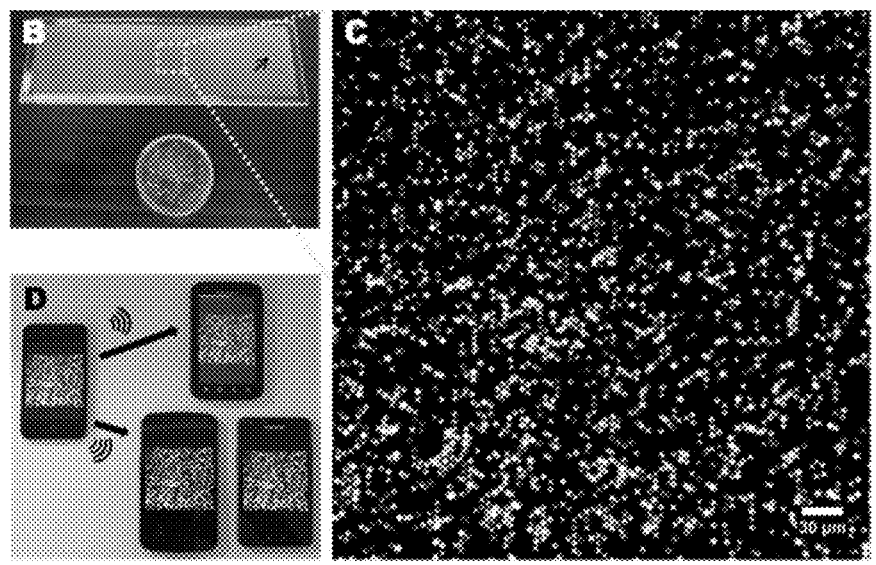
Figure 1

List of DNA sequences and their corresponding barcodes.

| Disease/ Biomarker | Capture Name/ Sequence (5' to 3') | Target Name/ Sequence (5' to 3') | Secondary Probe Name/ Sequence | Corresponding Barcode | Corresponding Barcode Spectrum |
|---|---|---|---|---|---|
| Influenza<br><br>Hemagglutinin – Influenza Type A (H1N1) | C1<br><br>CCG TCT TAG TTT GCA TAG TTT CCC GTT ATG | T1<br><br>CGG CGA TGA ATA CCT AGC ACA CTT A CTA CA TAA CGG GAA ACT ATG CAA ACT AAG AGG G | D<br><br>5'-Alexa647-TAA GTG TGC TAG GTA TTC ATC GCC G-3' | B1 | |
| Influenza<br><br>Neuraminidase – Influenza Type A (H3N2) | C2<br><br>ACT TGG TTG TTT GGG GGG GAG TTG AAT TCA | T2<br><br>CGG CGA TGA ATA CCT AGC ACA CTT A CTA TG AAT TCA AGT CCC CCG CAA ACA ACC AAG T | | B2 | |
| Influenza<br><br>Hemagglutinin – Influenza Type A (H5N1) | C3<br><br>CCA TTC CCT GCC ATC CTC CCT CTA TAA AAC | T3<br><br>CGG CGA TGA ATA CCT AGC ACA CTT A CTA GT TTT ATA GAG GGA GGA TGG CAG GGA ATG G | | B3 | |
| Hepatitis B (HBV)<br><br>PB-2 – HBV | C4<br><br>TCA GAA GGC AAA AAA GAG AGT AAC T | T4<br><br>CGG CGA TGA ATA CCT AGC ACA CTT A CTA AG TTA CTC TCT TTT TTG CCT TCT GA | | B4 | |
| Hepatitis C (HCV)<br><br>KY 150 – HCV | C5<br><br>CAT AGT GGT CTG CGG AAC CGG TGA GT | T5<br><br>CGG CGA TGA ATA CCT AGC ACA CTT A CTA AC TCA CCG GTT CCG CAG ACC ACT ATG | | B5 | |
| Negative Control | C6<br><br>GAC AAT GCT CAC TGA GGA TAG T | T6<br><br>CGG CGA TGA ATA CCT AGC ACA CTT A CTA AC TAT CCT CAG TGA GCA TTG TC | | B6 | |
| Positive Control | C7<br><br>CCA ATA TCG GCG GCC | T7<br><br>CGG CGA TGA ATA CCT AGC ACA CTT A CTA GG CCG CCG ATA TTG G | | B7 | |

Figure 8

WIRELESS COMMUNICATION DEVICE-BASED DETECTION SYSTEM

CROSS REFERENCE TO RELATED APPLICATIONS

This application is a national stage application under 35 U.S.C. 371 of International Application No. PCT/CA2013/050953 filed Dec. 11, 2013, which in turn claims the benefit under 35 U.S.C. 119(e) of U.S. Provisional Ser. No. 61/735,847, filed Dec. 11, 2012, the contents of each of which are hereby incorporated by reference into the present disclosure.

REFERENCE TO SEQUENCE LISTING SUBMITTED VIA EFS-WEB

This application includes an electronically submitted sequence listing in .txt format. The .txt file contains a sequence listing entitled "0180354.0029 ST25.txt" created on Apr. 30, 2019 and is 3,842 bytes in size. The sequence listing contained in this .txt file is part of the specification and is hereby incorporated by reference herein in its entirety.

FIELD OF THE INVENTION

The present disclosure relates to the field of information management, target detection and decision support, and more specifically, to a system and a method of combining barcode technology with wireless communications devices, such as smartphones, tablets, personal device assistant, or computer technology, to acquire and analyze and transmit data. Particularly, the present invention combines barcode technology with wireless communication device technology to engineer a chip-based multiplex detection system to analyze and track the presence of disease markers, pathogens, contaminants, or other organic or inorganic targets of interest and transmit collected data wirelessly to a designated location or to multiple locations.

BACKGROUND OF THE INVENTION

Advances in internet technology, social media, and smartphones have significantly changed how the global population communicates. Information pertaining to events occurring in one part of the world can be globally transmitted instantaneously. Yet, these emerging communication strategies have not been fully integrated with detection devices to simplify the detection process and enable global surveillance of pathogens, disease markers, contaminants, or other organic or inorganic targets of interest. In a disease-relevant example, much of the population in the world lives in resource-poor settings where emerging molecular detection systems are not available because of cost constraints, the need for stable and complex infrastructure, device size, and the requirement for skilled technicians to interpret the diagnostic results (1-3). Consequently, undiagnosed or misdiagnosed diseases can spread and become drug resistant, leading to economic burden, morbidity, and mortality. The integration of wireless communications devices such as smartphones—whose subscription reached over 5.9 billion worldwide in 2011 (4)—and tablets with state-of-the-art multiplexing detection devices would alleviate these problems and enable the real-time global surveillance of disease or contamination spread.

Thus far, "smart" mobile devices such as smartphones have only been used for imaging the test lines on lateral flow immunoassays, bacteria labeled with fluorophores, and tissue stains (5-7). These imaging techniques, however, cannot detect the early stages of infection or contamination because of poor analytical sensitivity and are incapable of detecting different strains or pathogens in a high throughput manner because of their inability to detect multiple biomarkers simultaneously. To overcome these limitations, there has been effort to combine cell phone technology with simple point-of-care devices such as lateral flow immunoassays and molecular pathology (4-8). But these techniques have poor analytical sensitivity and limited multiplexing capabilities. Despite the disclosures in the literature of combining smart phones and imaging techniques, there remains a greater challenge in coupling wireless communication device technology such as smartphones and tablets with more complex target detection schemes that can increase the throughput of the detection process and are capable of simultaneously detecting multiple targets such as pathogen or contaminant strains or mutations.

One example of barcode technology, quantum dot (QD) barcode technology, is versatile in molecular detection and can detect a variety of targets, including both genomic or proteomic targets (12-14). Each barcode may include a unique optical signature due to the incorporation of different emitting QDs within, for example, a microbead to create a barcode. The barcode is then conjugated with a ligand that can specifically bind to and recognize a target of interest, such as a molecule, pathogen marker, a contaminant, or a whole pathogen. Whereas the barcode (the primary label) identifies the target of interest, the binding of a secondary label onto the target indicates the successful capture of the target by the barcode ligand. An optical signature comprised of the primary label/barcode signal and the secondary label signal indicates positive detection of the target of interest from a sample. A challenge to using these barcodes in point-of-care detection is that a skilled technician is required to run the assay because subtle differences in microbead number, incubation time, and microbead stability can influence the analytical performance. The ability to assemble these barcodes on a chip would alleviate these problems. Microbeads assembled on a chip are currently used in sequencing analysis but the cost of the final chip is high because the microbeads are assembled on the ends of optical fibers (15). Therefore, current assembling techniques of fluorescent microbeads are not cost-effective for conventional detection applications in remote or resource-limited settings.

There are currently no systems that combine wireless communications devices with barcoding technology that can effectively detect multiple targets of interest simultaneously. In particular, there is currently no system that combines wireless communications devices with barcoding technology that can effectively and simultaneously detect multiple contaminants or pathogens and differentiate between contaminants or species of pathogens. Therefore, one objective of the present invention is to provide a system that combines barcoding technology and portable wireless communications device technology to simultaneously detect multiple targets such as contaminants, disease markers, pathogens, mutations, peptides, genomic targets, polysaccharides and other organic or inorganic targets that may be of interest.

A further object of the invention is to provide a system and method that combine portable wireless communication device technology and barcode technology and that the system and method are suitable for collecting information from a sample, analyzing the information and using the analysis to simultaneously identify multiple targets of interest.

A further object of the invention is to provide a system and method that combine portable wireless communication device technology and barcode technology and that the system and method are capable of transmitting the collected information wirelessly to a remote site for storage or further analysis of the information.

Further and other objects of the invention will be realized from the following Summary of the Invention, the Discussion of the Invention and the embodiments and Examples thereof.

SUMMARY OF THE INVENTION

Within the present invention, systems and methods are provided that combine wireless communication devices with a barcoding multiplex detection system, such as quantum dot barcoding, to enable the simultaneous detection of multiple organic and inorganic targets of interest including pathogens, pathogen markers, peptides, proteomic and genomic targets, polysaccharides, organic and inorganic molecules and so forth in a sample. The systems of the present invention allow for the quantitative analysis of multiple targets of interest using a portable wireless communication device having a camera to image the optical signal from the multiplex detection system. The wireless capabilities of systems and methods of the present invention allow them to be used in remote settings, enable wireless transmission of the collected data and results for storage and/or further interpretation at remote locations, and allows the mapping and surveillance of the targets. Further, the systems and methods of the present invention allow global surveillance of pathogen or contaminant dispersion and migration in real-time and can potentially simplify epidemiological mapping.

In one embodiment, the present invention relates to a detection system for simultaneous identification of multiple targets of interest. The system, in one embodiment, includes: (a) a multiplex detector comprising different populations of primary labels and secondary labels, each population of primary labels being bound to a ligand specific to one of the targets of interest, each population of primary labels being capable of emitting a first signal corresponding to the bound target-specific ligand when exposed to an excitation source, and the secondary labels being capable of binding to a target-specific ligand and of emitting a second signal when exposed to the excitation source, the combination of the first and second signals of one population producing an overall signal in the presence of a target of interest; and (b) a portable wireless communication device comprising: (i) an image capturing means for capturing the first and second signals, and (ii) a processing means for analyzing the captured signals, whereby identification of a target of interest occurs when the overall signal corresponding to said target is captured.

In one embodiment of the system of the present invention the primary and secondary labels comprise barcodes, metal, semiconductor or organic based nanostructures or molecules, organic dyes, or a combination thereof.

In another embodiment of the system of the present invention the ligands include nucleotide-based ligands, amino acid-based ligands, polysaccharide-based ligands, protein based ligands, antigens, antibodies, and hormones, or other organic or inorganic molecules.

In another embodiment of the system of the present invention the first and second signals are optical signals, and wherein the system further comprises an excitation source for exciting the primary and secondary labels, and an optical means for collecting emission optical signals from the excited primary and secondary labels.

In another embodiment of the system of the present invention the first and second signals are optical signals, and wherein the portable wireless communication device further comprises an excitation source for exciting the primary and secondary labels and an optical means for collecting emission optical signals from the excited primary and secondary labels.

In another embodiment of the system of the present invention the primary label is a barcode.

In another embodiment of the system of the present invention the barcodes are coupled to a static substrate or flow in solution through a dynamic substrate.

In another embodiment of the system of the present invention the substrate is a static substrate comprising a surface having (i) a plurality of indentations capable of receiving the multiplex detection system, or (ii) a substantially flat surface onto which the multiplex detection system is deposited In another embodiment of the system of the present invention the substrate is a static substrate selected from the group consisting of glass, paper, cellulose or plastic.

In another embodiment of the system of the present invention the substrate is a dynamic substrate, the dynamic substrate comprising micro channels or capillary networks.

In another embodiment of the system of the present invention the substrate comprises a surface having a plurality of indentations capable of receiving the populations of barcodes and secondary labels, or a substantially flat surface onto which the barcodes and secondary labels are deposited.

In another embodiment of the system of the present invention the first and second signals are optical signals, and wherein the system further comprises an objective means for collecting the first and second optical signals.

In another embodiment of the system of the present invention the wireless communication device includes communication means for (i) sending captured signals through a network system, (ii) sending the analysis of the captured signals through a network system, or (iii) sending both the captured signals and the analysis of the captured signals through a network system, to a remote location.

In another embodiment of the system of the present invention the analysis of the captured signals includes quantification of the multiple targets in the sample.

In another embodiment of the system of the present invention the multiple targets include unicellular and multicellular microorganisms, inorganic molecules and organic molecules.

In another embodiment of the system of the present invention the organic molecules include peptides, proteins, oligosaccharides, lipids, genes, nucleic acid sequences, amino acid sequences, RNA sequences and DNA sequences and wherein inorganic molecules contain metal atoms.

In another embodiment of the system of the present invention the image capturing means is a camera that can image the signals from the primary and the secondary labels.

In another embodiment of the system of the present invention the processor means includes instructions that, when executed, operate to cause the processing means to differentiate the first and second signals such as to identify the target or targets of interest in a sample and quantify said target or targets.

In another embodiment of the system of the present invention the barcodes comprise quantum dots.

In another embodiment of the system of the present invention the portable wireless communication device is a smart phone, a computer, a tablet, or a watch.

In one embodiment, the present invention relates to a method for simultaneously detecting the presence of multiple targets of interest in a sample, the method including: (a) contacting the sample with a multiplex detection system, the multiplex detection system capable of producing different signals upon interaction with the multiple targets of interest, each signal corresponding to one of the multiple targets; (b) collecting the signals via a portable wireless communication device; and (c) analyzing the collected signals using the portable wireless communication device to identify the presence of the multiple targets of interest in the sample.

In one embodiment of the method of the present invention, the multiplex detection system comprises different populations of primary labels and secondary labels for each of the multiple targets of interest, each population of primary labels being bound to a ligand specific to one of the multiple targets of interest, each population of primary labels being capable of emitting a first signal corresponding to the bound target-specific ligand when exposed to an excitation source, and the secondary labels being capable of binding to a target-specific ligand and of emitting a second signal when exposed to the excitation source, the combination of the first and second signals of each population producing an overall signal in the presence of a target of interest, and wherein prior to step (b) the method further comprises exposing the multiplex detection system with the sample to the excitation source to produce different populations of first and second signals corresponding to the targets of interest, whereby the presence of one target in the sample is identified when the overall signal corresponding to said one target is collected.

In another embodiment of the method of the present invention prior to the exposure to the excitation source said method further includes at least one washing step to remove unbound materials.

In another embodiment of the method of the present invention the analysis of step (c) includes quantifying the multiple targets in the sample.

In another embodiment of the method of the present invention the primary and secondary labels comprise barcodes, metal, semiconductor or organic based nanostructures and molecules, organic dyes or a combination thereof.

In another embodiment of the method of the present invention the ligands include nucleotide-based ligands, amino acid-based ligands, polysaccharide-based ligands, protein based ligands, antigens, antibodies, and hormones and other organic and inorganic molecules.

In another embodiment of the method of the present invention the primary label is a barcode.

In another embodiment of the method of the present invention the barcodes are coupled to a static substrate or flow in solution through a dynamic substrate.

In another embodiment of the method of the present invention the substrate is a static substrate including a surface having (i) a plurality of indentations capable of receiving the multiplex detection system, or (ii) a substantially flat surface onto which the multiplex detection system is deposited.

In another embodiment of the method of the present invention the substrate is a static substrate selected from the group consisting of glass, paper, cellulose or plastic substrate.

In another embodiment of the method of the present invention the substrate is a dynamic substrate, the dynamic substrate comprising micro channel or capillary networks.

In another embodiment of the method of the present invention step (b) includes: (i) collecting the signals at a first end, and (ii) sending the signals to a second end through a network system; and wherein step (c) includes analyzing the signals at the first end, at the second end or at both the first and the second ends.

In another embodiment of the method of the present invention the second end is a remote location from the first end.

In another embodiment of the method of the present invention the second end includes multiple remote locations from the first end.

In another embodiment of the method of the present invention the multiple targets include unicellular and multicellular microorganisms, inorganic molecules and organic molecules.

In another embodiment of the method of the present invention the organic molecules include peptides, proteins, oligosaccharides, lipids, genes, nucleotide sequences, amino acid sequences, RNA sequences and DNA sequences and wherein inorganic molecules include metal ions.

In one embodiment, the present invention relates to an assembly of barcodes for simultaneously detecting multiple targets of interest, the assembly of barcodes including: (a) a substrate having a surface; and (b) different populations of barcodes coupled to the surface, each population of barcodes having a ligand specific to one of the multiple targets.

In one embodiment of the assembly of barcodes of the present invention, the assembly is portable.

In another embodiment of the assembly of barcodes of the present invention the surface of the substrate comprises a plurality of indentations capable of receiving the multiplex detection system.

In another embodiment of the assembly of barcodes of the present invention the surface of the substrate comprises a substantially flat surface onto which the multiplex detection system is deposited In another embodiment of the assembly of barcodes of the present invention the substrate is a static substrate selected from the group consisting of glass, paper, cellulose or plastic substrate.

In one embodiment, the present invention is a method of manufacturing an assembly of barcodes for simultaneously detecting multiple targets, the method including: (a) providing a substrate having a surface capable of barcode deposition; (b) contacting the surface of the substrate of the substrate with different populations of barcodes, and (c) allowing the different populations of barcodes to adhere to the surface of the substrate.

In one embodiment of the present invention the substrate of the above embodiments includes a substantially flat surface capable of barcode deposition.

In another embodiment of the present invention, the substrate of the above embodiments includes a plurality of microwells or indentations capable of receiving the barcodes.

In another embodiment of the present invention the substrate of the above embodiments is a static substrate selected from the group consisting of glass, paper, cellulose or plastic substrate.

BRIEF DESCRIPTION OF THE DRAWINGS

Embodiments will now be described, by way of example only, with reference to the drawings, in which:

FIG. 1: (A) Graph illustrating an overview of a barcode/portable wireless communications device system in accordance to one embodiment of the present invention. In the embodiment illustrated in panel A, the system includes microwell chip having different quantum dot barcodes (after hybridization with a sample), an optical means for visualizing the signals emitted by the different quantum dot barcodes (the primary label) and secondary labels, and a portable wireless communications device for capturing the signals from the optical means and for analyzing the signals, and a centralized facility that may wirelessly receive the signals from the portable wireless communications device for storage and for further analysis. (B) Is a photograph of a microwell chip with different barcodes in each well. (C) is a microphotograph taken with a portable wireless communications device camera depicting the image of five different quantum dot barcodes (originally in color) assembled on the surface of the chip. These barcodes are excited with Hg lamp ($\lambda ex=350/50$), optical signal collected by a 20× objective (NA=0.50), filtered with 430 nm long-pass filter, and imaged using an Apple iPhone™ 4S smartphone with an exposure time of 0.05 s. (D) Photograph that illustrates the wireless transmission of the optical image taken by the smart phone of panel C (left side of panel D) to other devices.

FIG. 8 is a table listing DNA sequences and their corresponding barcode images and the corresponding barcode spectra.

DETAILED DESCRIPTION OF THE INVENTION

Figure 2:
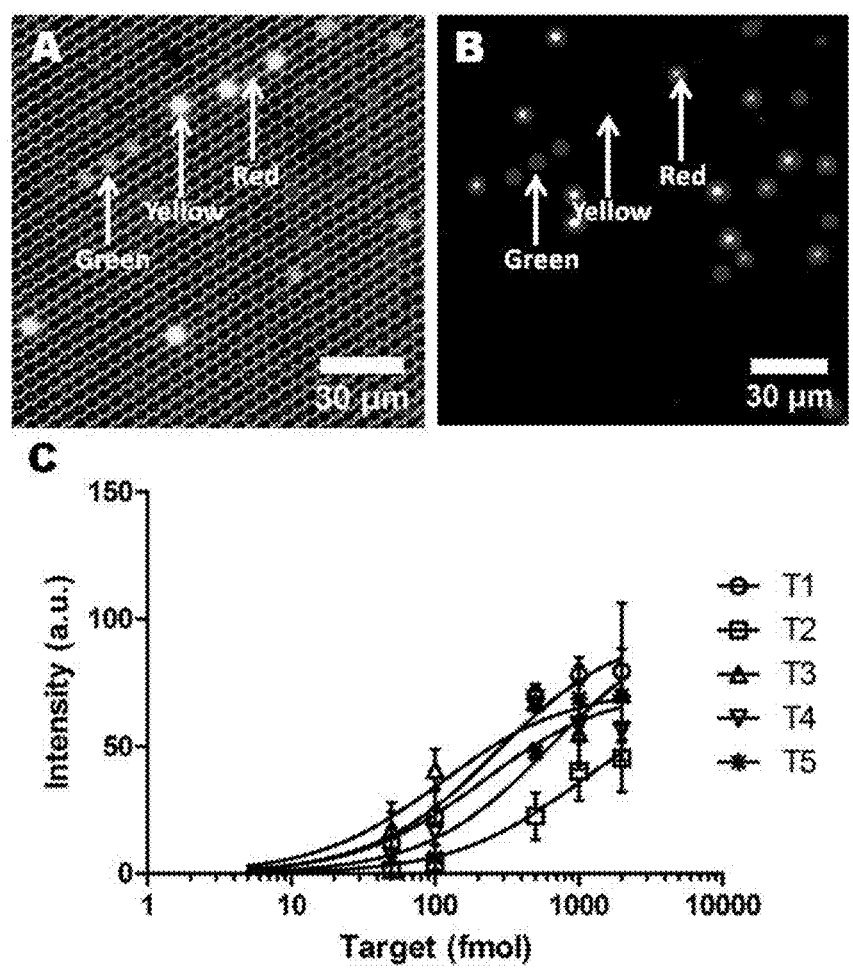
FIG. 2 shows images of assays and sensitivity curves. (A) microphotograph of green, yellow, and red barcodes (originally in color with examples highlighted using arrows, identified as B1, B4, and B6 in FIG. 8, respectively) deposited on the chip and imaged using an iPhone™ 4S smartphone camera (fluorescence microscopy parameters: objective of 20× at NA=0.50, $\lambda ex=350/50$, $\lambda em=430LP$, exposure time=0.05 s). The microwells are visualized using brightfield microscopy. The fluorescence and brightfield images are super-imposed. (B) After the assay, the wireless communications device camera-acquired fluorescence image of the microbead barcodes are bound with the target analyte and secondary labeled probe (fluorescence microscopy parameters: objective of 20× at NA=0.50, $\lambda ex=640/40$, $\lambda em=692/40$, exposure time=1 s). Both green and red beads (originally in color) are present, but not the yellow beads (examples highlighted using arrows). This demonstrates that T1 and T6 genomic targets are present in the sample but not T4. Of note, the white spots on the barcodes are due to overexposure from the high combined intensity of the Alexa647 fluorophore and the 640 nm quantum dots impregnated within B6. (C) Sensitivity curves for genetic biomarkers for the influenza A viruses H1N1 (T1), H3N5 (T2), and H5N1 (T3), and hepatitis B 420 (T4) and C (T5) used here only as examples of infectious disease applications. All error bars were calculated based on the standard deviation from three replications.

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

The singular form "a", "an", and "the" includes plural references unless the context clearly dictates otherwise.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "ligand" or "probe" as used herein refers to a capture molecule, organic or inorganic, or group of molecules that exhibits selective and/or specific binding to one or more organic or inorganic targets. Targets may include specific sites of a receptor, a probe, another molecule (organic or inorganic) or target or whole microscopic organisms (unicellular or multicelluar) such as a pathogen. There can exist more than one ligand for a given target. The ligands may differ from one another in their binding affinities for the target. Examples of ligands include nucleotide-based ligands (aptamers, oligonucleotides, and so forth), amino acid-based ligands (antibodies, peptides, proteins, enzymes, receptors and so forth), polysaccharide-based ligands (for example hyaluronan), antigens, hormones, including peptide-hormones, lipid/phospholipid-hormones and monoamine hormones, and any other molecule capable of binding to an organic or inorganic target.

Multiplex may be understood as the ability to detect the presence—of more than one target simultaneously. The multiplex detection system may include barcodes, metal, semiconductor, or organic based nanostructures or molecules, (e.g. organic dyes).

Barcodes may include any type of structure or system that allows a target to be distinguished. Barcodes that may be used with the present invention include magnetic, optical (i.e. quantum dots, organic dyes), electrical, DNA and Lithographic barcodes.

As used herein, a "quantum dot" (QD) is a semiconducting photoluminescent material, as is known in the art (For example, see Alivasatos, Science 271:933-937 (1996)). Non-limiting examples of QDs include: CdS quantum dots, CdSe quantum dots, CdSe/CdS core/shell quantum dots, CdSe/ZnS core/shell quantum dots, CdTe quantum dots, PbS quantum dots, and/or PbSe quantum dots. As is known to those of skill in the art, CdSe/ZnS means that a ZnS shell is coated on a CdSe core surface (ie: "core-shell" quantum dots). The shell materials of core-shell QDs have a higher bandgap and passivate the core QDs surfaces, resulting in higher quantum yield and higher stability and wider applications than core QDs.

Quantum dot barcodes refers to microbeads containing different combinations of fluorescent semiconductor nanocrystals. Each microbead may include a unique optical signature that identifies the surface conjugated molecule. Approximately 10,000 to 40,000 different optical barcodes may be engineered using 5-6 different color quantum dots and six intensity levels (9). This enables significant multiplexing and these barcodes can detect targets in a flow cytometer (10-13) or microfluidic channel (14, 15) as well as through other means.

Wireless communication device refers to any device using radio-frequency, infrared, microwave, or other types of electromagnetic or acoustic waves in place of wires, cables, or fibre optics to transmit or receive signals or data, and that the device includes a camera for acquiring images, signals or data and electronic components to sustain analysis of the images, signals or data. Wireless communication devices include smart phones, tablets, smart watches, personal assistant devices, and portable computers.

The present invention demonstrates that the integration of a multiplex detection system, such as barcodes, with portable wireless communication devices, such as smartphone or tablet technology, may be used in a system for multiplex detection and identification of targets of interest and wireless transmission of data. The detection device contemplates integrating a portable wireless communications device with the multiplex detection system where the optics, excitation source, and detector may be combined into a single device the size of the current smartphone or tablet.

With reference to FIG. 1 A, in one embodiment, the system 100 may include a substrate 120 for receiving the multiplex detection system thereon, and a wireless communication device 130. As illustrated in FIG. 1 A the multiplex detection system may include a primary label 110, a secondary label 112 and a ligand 111 to a target of interest coupled to the primary label 110 and secondary label 112. The secondary label may be coupled to the same target-specific ligand as the one bound to the primary label, or to another target-specific ligand. In FIG. 1, the primary label 110 is represented as quantum dot barcodes. It should be understood that other multiplexing systems may be used and that primary labels other than QD barcodes may be used. The system may also include an excitation source 140 for exciting the primary label 110 and secondary label 112, an optical means having an objective 150 for collecting the optical emission from the excited primary label and secondary label, one or more filters 142, 144 for filtering the beams from the excitation source and the emissions from the primary label and secondary label. The system 100 may also include a centralized facility 160 for wirelessly receiving the data collected by the wireless communication device 130 for storing or further analyzing the data collected.

Examples of excitation sources that may be used with the system of the present invention may include light emitting diodes, laser diodes, lasers, and lamp burners. Examples of non-light emitting excitation sources include electrical potential sources. Examples of optical filters that may be used with the system of the present invention may include absorbing glass filters, dye filters, color filters, dichroic mirrors, beam splitters, and thin-film polarizers.

In one embodiment of the present invention, the wireless communication device itself may include at least one of the excitation source, the objective for collecting the emission from the excited barcodes and secondary labels and one or more filters.

Figure 9:
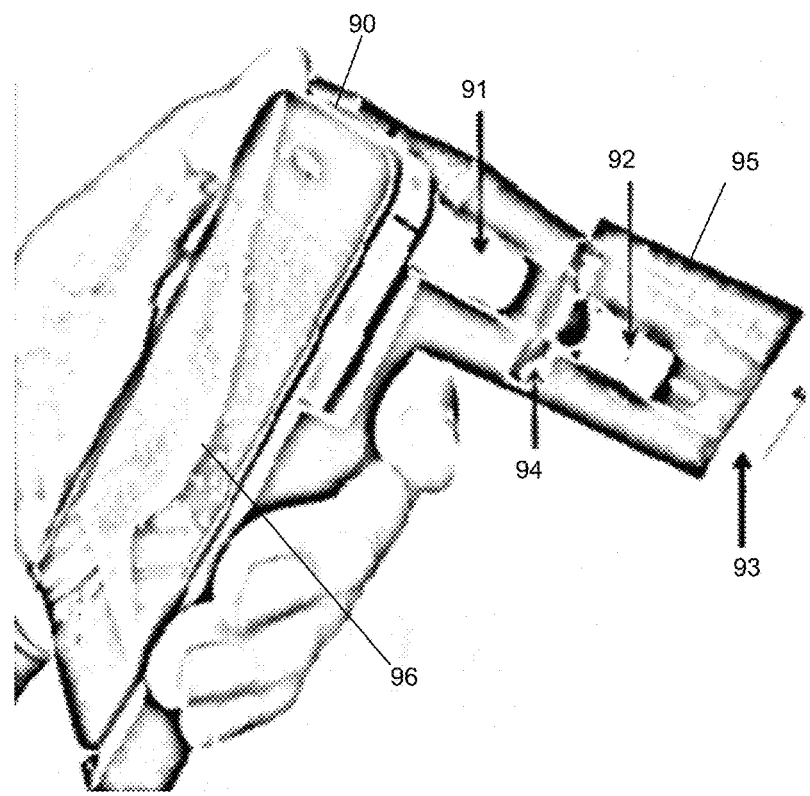
FIG. 9 is a graph illustrating a portable detection system in accordance to one embodiment of the present invention.

FIG. 9 illustrates a portable detection system comprising a substrate 93 placed on the surface of a stage 95 having different quantum dot barcodes, an objective lens 92 for collecting the emissions emitted by the quantum dot barcodes, a filter 94 for filtering the emissions from the substrate, an eye piece 91 for collecting the filtered emissions, and a wireless communication device 90 attached to an eye piece 91 for receiving the filtered emissions and imaging such emissions. The optical image 96 taken from the substrate is shown on the wireless communication device.

The substrate may be any suitable substrate for receiving the multiplex detection system and that can be portable. Substrates can be static or dynamic. A static substrate may include a substantially flat surface capable of receiving the multiplex detection system or capable of barcode deposition. Substrates may include glass slides, cellulose membranes, paper, plastic membranes or slides and so forth. A dynamic substrate may include a micro-channel or capillary network. For convenience, the static substrate may also include one or more wells that may help organize the multiplex detection system. The wells may also serve to hold the multiplex system on the substrate. In the case of a static substrate the multiplex detection system may be coupled to a surface of the substrate. In the case of a dynamic substrate, the multiplex detection system may flow in solution through the substrate.

With reference to FIG. 1 A, toward the development of such a system 100 for multiplex detection and/or identification and wireless data transmission, engineering a multiplex-chip platform, which may be portable, may be manufactured by assembling primary labels, such as barcodes 110 on the surface of a microfabricated substrate 120, such as a slide. The substrate depicted in FIG. 1 A includes a plurality of indentations or microwells 115 for receiving the primary labels and secondary labels. Samples may be added to the substrate 120, and a wireless communication device 130 may be used to collect or capture signals 125 from the substrate 120, deconvolve the signals and associate the signals with a specific target, such as a pathogen, disease marker, or contaminant.

Ligands or probes that are specific to different targets of interest may be conjugated or attached onto a primary label, such as a barcode, and to a secondary label. The conjugation or attachment of a ligand or probe to a barcode or a secondary label will depend on the type of ligand or probe used and the surface chemistry of the barcode and secondary label. Examples of conjugation techniques include carbodimmide mediated, maleimide, n-hydrosuccinimide or thiol-metal chemistry, DNA-hybridization, antigen-to-antibody, protein-to-small molecule (streptavidin-to-biotin). By way of example, oligonucleotide-based ligands or probes may be conjugated onto the surface of each barcode using carbodiimide chemistry.

Figure 4:
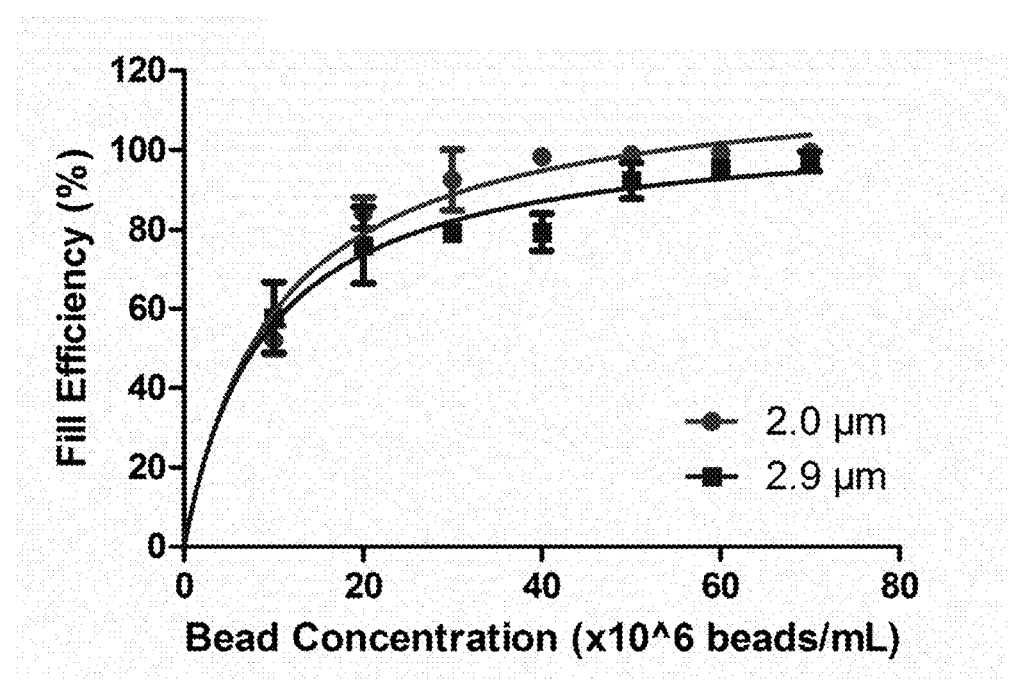
FIG. 4 is a graph illustrating microbead barcode filling efficiency of a microwell chip as determined by the concentration and size of the microbeads for 2.0 µm (circle) and 2.9 µm (square) in accordance to one embodiment of the present invention.

With continued reference to FIG. 1A, the barcodes 110 with the conjugated ligand 111 may then be arranged onto microfabricated chips or substrates 120 including a plurality of indentations 115. The indentations may be 3 µm-diameter wells (MicroPep). Barcodes beads may be prepared by using any technique known in the art, for example the technique of flow-focusing (16). The barcode beads may be of any suitable size. For example, they may be of a size similar to the diameter of the microwells. A solution, preferably a buffer solution, including a panel of barcodes may be added directly onto the chip. The barcodes may then be allowed to settle into each well. These microbeads may not easily desorb off of the chip during subsequent assays after they are bound to the microchip. As illustrated in FIG. 4, the filling efficiency on the chip is determined by the concentration and size of the beads. In our assays, we typically use a filling efficiency of 25 to 50% to maximize access of the capture molecule to the bead surface. FIG. 1B is a photograph of a typical microwell chip containing different barcodes in each well. The black arrow illustrates a drop of a sample to be analyzed on the chip. The sample may be allowed to incubate at about room temperature or more. The chip may then be rinsed and imaged using the wireless communication device. FIG. 1 C is a micrograph of the image captured by a wireless communication device of quantum dot barcodes assembled on the surface of a chip.

In another embodiment, the system of the present invention may be used in a method for simultaneously detecting multiple targets of interest in a sample. In one embodiment, the method may include: (a) contacting the sample with a substrate having a multiplex detection system distributed therein, the multiplex detection system being capable of producing different signals upon interaction with the multiple targets, each signal corresponding to a particular target; and (b) collecting the signals from the substrate with a wireless communication device, and (c) analyzing the collected signals using the wireless communications device, whereby the multiple targets in the sample can be simultaneously detected. In one aspect of the present invention the analysis of step (c) includes quantifying the multiple targets in the sample.

The applicants developed a simple method to assemble a primary label, such as microbead barcodes, on the surface of a chip. In one embodiment, glass slides may be microfabricated with 3.0 µm-diameter indentations. A solution of microbead barcodes, which may be about 3.0 µm sized microbead, having different combinations of fluorophores may then be added to the chip. The microbead barcodes may settle into each microwell. Once bound to the microwell, these microbeads may not desorbed from the surface of the microwell. The microbeads may be held in place by non-covalent forces. The concentration and size of the barcodes may determine the filling efficiency (see FIG. 4).

With reference to FIG. 1 A, a sample of interest, such as a subject's biological fluid or an environmental sample, may be incubated on a chip 120 containing primary label 110, ligand 111 and secondary label 112 for a suitable amount of time, for example for about 20 minutes, rinsed or washed, and placed on the system for analysis. An excitation source 140 may then be used to excite the primary label and the secondary label. The optical signal may be collected by an objective. The optical signal may be filtered with one or more filters 142, 144 imaged using a wireless communications device camera 130, and analyzed using the wireless communications device 130 or remotely in a centralized facility 160 or by other wireless communication devices or both. In one embodiment of the present invention, the collected signal data may be interpreted as positive (+) or negative detection (−) using a custom-designed algorithm which may be integrated/downloaded/uploaded onto the wireless communications device. The data may be sent wirelessly to a centralized facility for further evaluation, storage, or for the mapping and tracking of pathogens or contaminants. Detection of a specific target occurs when the ligand binds the target and the overall signal of the microbeads comprises of both the primary label and the secondary label.

In one embodiment of the method of the present invention, a primary label may be bound to a first ligand and a secondary label may be bound to a second ligand, both ligands having affinity for the same target of interest. The first and the second ligand may be the same or different. After a suitable incubation time, a washing step may be added after the binding of a label to a ligand to wash away any unbound material. A sample of interest may then be incubated together with both the primary label bound to a target-specific ligand and with the secondary label bound to a target-specific ligand for a suitable incubation time. The incubation may be followed by at least one washing step to remove any unbound material. The washing step may then be followed by the excitation and analysis step.

In another embodiment, the secondary label may be added to the primary label bound to a ligand. Then a sample of interest may be incubated with the primary label bound to a ligand and with the secondary label for a suitable incubation time. A washing step to remove any unbound material may be performed after adding the sample. The excitation step may be performed after the washing step(s).

In another embodiment, a sample of interest may be incubated with the primary label bound to a ligand for a suitable amount of incubation time. A secondary label may then be added for a suitable incubation time. A washing step to remove any unbound material may be performed before adding the secondary label, after adding the secondary label or both before and after adding the secondary label. The excitation step may be performed after the washing step(s).

FIG. 1 B shows a microwell chip in accordance with one embodiment of the present invention, having different barcodes in each well. In a biological assay, the sample, for example about 10 µL, may be disposed or placed on the chip (see black arrow), incubated at 40° C., rinsed, and imaged. With reference to FIG. 1 C, a wireless communications device camera may capture the image of the different barcodes assembled on the surface of the chip (in the case of FIG. 1 C, five different QD barcodes). These barcodes may be excited a suitable excitation source such as a Hg lamp ($\lambda ex=350/50$). The optical signal may be collected by an objective. The optical signal may be filtered, for example with 430 nm long-pass filter, and imaged using a wireless communication device, such as an Apple iPhone™ 4S smartphone with an exposure time of 0.05 s. FIG. 1 D demonstrates the wireless transmission of the optical image to other wireless communication devices.

Advantages of the present invention include: (a) detection of one or multiple (i.e. more than one) targets (i.e. multiplexing) as compared to other cellphone-based approaches; (b) the deposition of barcodes on the chip, compared to those stored in solution, enables higher portability of barcodes and reduces the number of steps in the barcode assay process; (c) the device itself would also be portable (not much bigger than the size of a smartphone or tablet—to which it will be attached); (d) the current detection platforms for identifying quantum dot barcodes require expensive instruments and detectors and would be prohibitive in their use in remote and resource-limited settings and in the field (12, 13); (e) the systems and methods of the present invention are simple and easy to use because the procedures are few and uncomplicated, thus obviating the need for a skilled technician; and (f) detection is relatively quick (less than 30 minutes) from deposition of sample to obtaining results of the analysis.

In order to aid in the understanding and preparation of the present invention, the following illustrative, non-limiting examples are provided.

EXAMPLES

Quantum Dot Synthesis

In this embodiment, quantum dots (CdSeS alloyed-ZnS capped) of peak emission wavelength 540 nm ("QD540") were purchased from CytoDiagnostics and used as instructed. Quantum dots (QDs) of peak emission wavelengths 589 nm ("QD589") and 640 nm ("QD640") were synthesized and characterized according to published procedures (18-20) and stored in chloroform at room temperature until use. Other types of QD nanoparticles may also be used.

Quantum Dot Barcode Synthesis

In this embodiment, QD barcodes were prepared by mixing together the quantum dots (QD540, QD589, and QD640) in different ratios with a polymer-based solution. The polymer solution consisted of poly(styrene-co-maleic anhydride) (32%, cumene terminated) from Sigma-Aldrich dissolved in chloroform, with the polymer concentration at 4 wt %. The resultant quantum dot polymer solution was then introduced into a nozzle system from Ingeniatrics using a syringe pump from Harvard Apparatus at a rate of 0.9 mL/hour, as well as double-distilled (DD) water as the focusing fluid at a rate of 180 mL/hour. The nozzle system was then submerged inside a beaker partially filled with DD water. The polymeric barcode beads were synthesized in situ, and the beads formed a white colloidal suspension in the water. After synthesis, the valve was closed and the beads were stabilized by overnight stirring and then collected. The beads were filtered using 35 µm BD Falcon nylon mesh strainer cap, and characterized using an automated Beckman Coulter Vi-Cell counter, and stored in DD water at 4° C. until use. The quantum dot concentrations required for preparing the seven different barcodes are presented in Table 2.

Barcode Bead Deposition on Micro Well Chip

For high dispersion and microwell filling efficiency of the five barcode beads (B1, B3, B4, B5, B6 from FIG. 8) on a glass slide having a plurality of 3 µm-diameter wells (Micro-Pep), samples with concentration $3\times10^7$ bead/mL were prepared for each. Then, 2 µL of each sample was mixed with 35 µL of DD water and 5 µL of DD water containing 1% Tween to produce a final mixture concentration of $6\times10^6$ beads/mL. The mixture was then sonicated for 5 minutes to reduce bead aggregation before depositing 30 µL of it on the microwell chip, which was rinsed with DD water and allowed to dry prior to deposition. The chip was then placed in an enclosed drying chamber containing dessicant to prevent dust particle contamination, and then allowed 2 hours to dry before imaging. Note that increasing the bead concentration in the mixture increases the microwell fill efficiency (FIG. 4), but with greater potential for aggregation.

Barcode Bead Conjugation and Validation

Conjugation of DNA capture strands (i.e. amine groups present on the 5' end of C1 to C7) to their corresponding barcode beads (i.e. carboxylic acid groups present on the polymeric 170 surface of B1 to B7) was done through reaction with 1-ethyl-3-(3-dimethylaminopropyl) carbodiimide hydrochloride (EDC). DNA capture strands from Bio Basic Inc., purchased HPLC-purified and used without further purification, were designed with an amine group and 12 base spacers on the 5' end. They were first prepared at a concentration of 10 pmol/µL in TE buffer and stored at 4° C. until further use. To conjugate, EDC was first dissolved in MES buffer (pH 5, 100 mM) at a concentration of 100 mg/mL. Approximately 106 beads were mixed with 100 µL of the EDC solution, and it was allowed to activate the bead carboxyl groups for 10 minutes. Then, 2.88 µL of the DNA capture strand solution, corresponding to 28.8 pmol of DNA, was added to the bead solution. The reaction was allowed to take place overnight.

Figure 7:
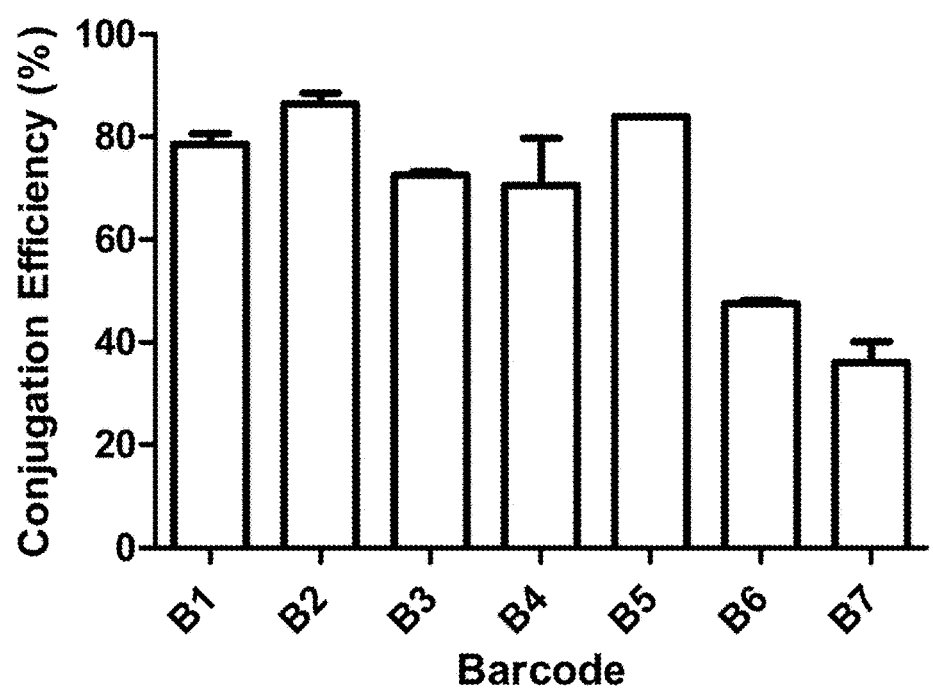
FIG. 7 is a graph illustrating capture strand conjugation efficiency for each barcode. Error bars were calculated based on the standard deviation from two replications.

To validate the conjugation, 1 µL of DD water containing 5% Tween was added to the 180 bead solution, centrifuged at 3000 g for 5 minutes. Then, 50 µL of the supernatant was extracted. The same conjugation procedures described above were performed for the control cases for each barcode (i.e. no conjugation), except DD water was added in place of beads. In a black 96-well plate, 10 µL of the supernatants from all seven conjugation cases, 10 µL of the supernatants from all seven control case, as well as 10 µL of four blank cases containing only DD water, were each added to individual wells. SYBR green I from Invitrogen, dissolved in DMSO, was first diluted to 1:10000 dilution by adding 1 µL of it to 10 mL of TE buffer, then 190 µL of the dilution was added to each of the sample-containing wells. All reactions were incubated at room temperature for 15 minutes before being read using a plate reader from BMG Labtech. Amount of conjugation for each barcode was then determined by comparing the fluorescence of the conjugation cases with their respective controls containing no beads. That is, lower signal indicates higher amount of conjugation. Results were converted to efficiency in percentages (see FIG. 7).

To finish the conjugation process, after the 50 µL of the supernatant was extracted for validation, the remaining supernatant was removed. Then, the conjugated beads were washed 195 twice with 100 µL of DD water containing 0.05% Tween and centrifuged at 3000 g for 5 minutes to remove any non-conjugated DNA capture strands. The conjugated beads were then stored in 100 µL DD water containing 0.05% Tween at 4° C. until further use.

Sensitivity Assay

Figure 5:
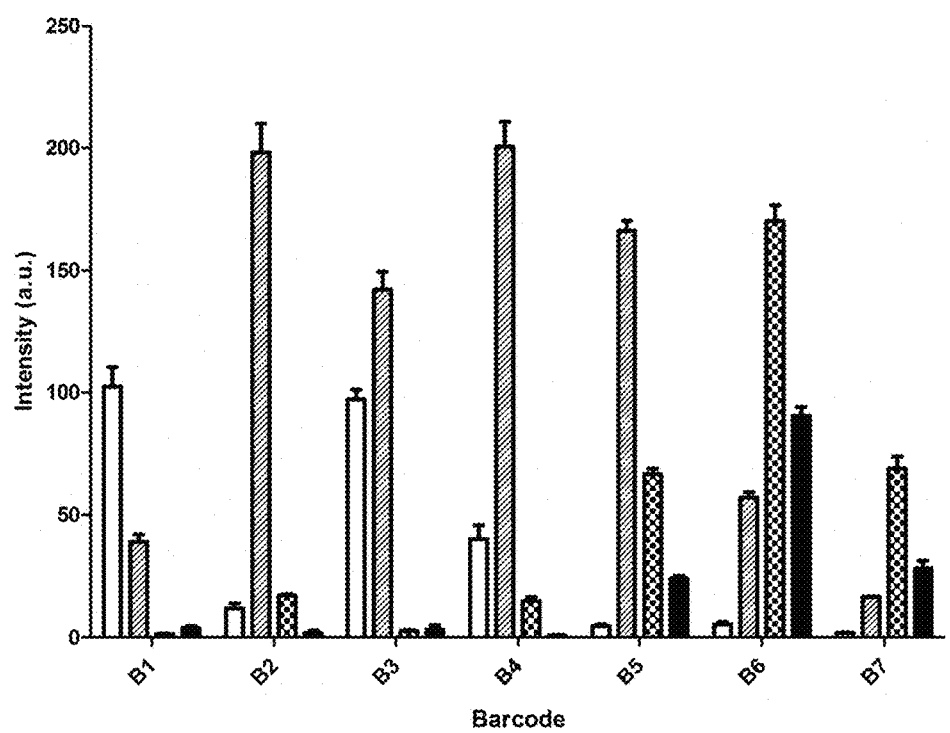
FIG. 5 is a graph illustrating intensities of quantum dot barcodes. Known barcode intensity profiles for all seven barcodes. From left to right, the bars represent intensity observed at the filter $\lambda em=530/10$ (white), $\lambda em=580/10$ (lined), $\lambda em=640/10$ (checkered), and $\lambda em=692/40$ (black). Error bars were calculated as the standard deviation from three replications.

Sensitivity assays were performed directly on the microwell chips for all infectious disease DNA target strands (T1 to T5 of FIG. 8) and their respective conjugated barcode beads (B1-C1 to B5-C5 of FIG. 8). The sensitivity results are illustrated in FIG. 5. DNA target strands from Bio Basic Inc., purchased HPLC-purified and used without further purification, were prepared in increasing concentrations of 0, 5, 10, 50, 100, 500, 1000, and 2000 fmol/µL in TE buffer. DNA detection strand from IDT DNA Technologies with Alexa647 fluorophore on the 5' end, purchased HPLC-purified and used without further purification, were prepared with concentration of 100 pmol/μL in TE buffer. Both DNA target and detection strand samples were stored at 4° C. until further use. To perform the assay, 1 μL of the conjugated bead sample, corresponding to approximately 104 conjugated beads, was deposited on a microwell chip for each assay condition and let dry for 1 hour. Then, 1 μL of each DNA target strand sample was mixed with 5 μL of hybridization buffer (10×SSC, 0.1% SDS, heated to 60° C.), 3 μL of DD water, and 1 μL of DNA detection strands or DD water (for the blank condition). This resulted in a total hybridization volume of 10 μL for each assay condition, which include blank, 0, 5, 10, 50, 100, 500, 1000, and 2000 fmol. The hybridization solution for each assay condition was deposited over the conjugated bead spots on the microwell chips and 215 incubated at 40° C. for 20 minutes. The microwell chips were then submerged in 10 mL of washing buffer (0.5×SSC, 0.1% SDS, heated to 40° C.), washed by agitation for 20 s, then let dry for 5 minutes before being imaged. Note that care must be taken so that the washing buffer does not dry and crystallize over the sample spots.

Multiplexing Assay

For the 3-plex multiplexing assay (FIGS. 2A and B), 2 μL of each conjugated barcode sample (B1-C1 (green), B4-C4 (yellow), and B6-C6 (red)), corresponding to approximately $2\times10^4$ barcodes each, were mixed together with 18 μL of DD water to produce a 4× dilution factor of the original. The dilution was to reduce bead aggregation after deposition on chip, which may confound barcode resolution during analysis. To perform the assay, 5 μL of the conjugated barcode mixture, corresponding to approximately $1.25\times10^3$ conjugated beads, was deposited on a microwell chip for each assay condition and let dry for 3 hours. Then, 2 μL of T1 and T6 (concentration of 2 pmol/μL each) was mixed with 40 μL of hybridization buffer (10×SSC, 0.1% SDS, heated to 60° C.), 14 μL of DD water, and 16 μL of the detection strand (concentration of 100 pmol/μL). This resulted in a total hybridization volume of 70 μL. From this, 10 μL of the hybridization solution was deposited over the conjugated barcode spots on the microwell chip and incubated at 40° C. for 20 minutes. The microwell chip was then submerged in 10 mL of washing buffer (0.5×SSC, 0.1% SDS, heated to 40° C.), washed by agitation for 20 s, washed again in another 10 mL of washing buffer to further reduce non-specific binding, then let dry for 5 minutes before being imaged. Note that care must be taken so that the washing buffer does not dry and crystallize over the sample spots.

Figure 3:
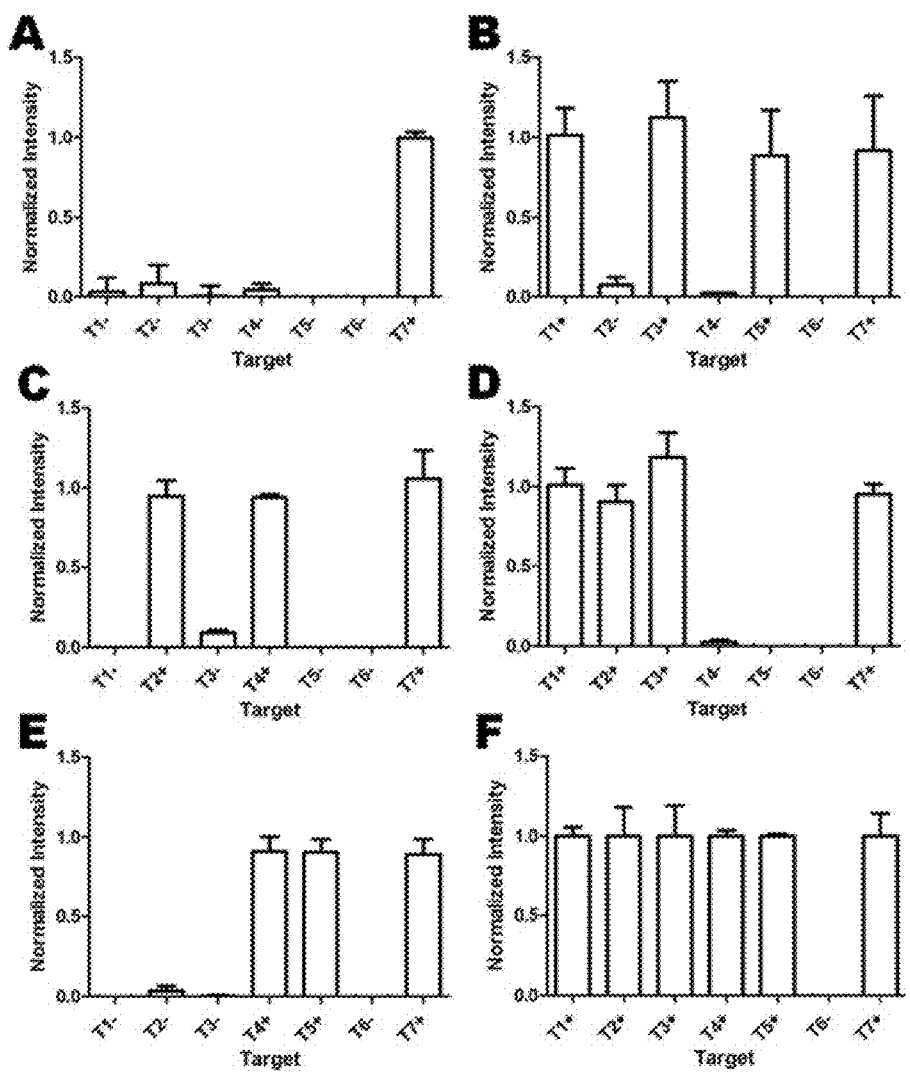
FIG. 3 illustrates multiplexed detection of five infectious disease target strands T1 to T5 used here only as examples of infectious disease applications as well as a negative control T6 and a positive control T7. (A) Only T7 was present during hybridization. (B) Targets T1, T3, T5, and T7 were present during hybridization. (C) Targets T2, T4, and T7 were present during hybridization. (D) Targets T1, T2, T3, and T7 were present during hybridization. (E) Targets T4, T5, and T7 were present during hybridization. (F) All targets except for T6 were present during hybridization. Note that except for T6, all other values in A-F were normalized to their respective positive values in F.

Cross reactivity between all five DNA target strands (T1 to T5) and their corresponding conjugated barcodes (B1-C1 to B5-O5), as well as negative and positive control cases (B6-C6 and T6, and B7-C7 and T7, respectively), was studied (FIG. 3 A-F). First, 6 μL of each conjugated barcode sample, corresponding to approximately $6\times10^4$ barcodes each, were mixed together with 126 μL of DD water to produce a 4× dilution factor of the original. The dilution was to reduce bead aggregation after deposition on chip, which may confound barcode resolution during analysis. To perform the assay, 8 μL of the diluted conjugated barcode mixture, corresponding to approximately $2\times10^4$ conjugated beads, was deposited on a microwell chip for each multiplexing case and let dry for 4 hours. Then, 2 μL of each target case (DD water for the negative conditions, and corresponding DNA target strand sample with concentration of 2 pmol/μL for the positive conditions) was mixed with 35 μL of hybridization buffer (10×SSC, 0.1% SDS, heated to 60° C.), 14 μL of DD water, and 7 μL of the detection strand (concentration of 100 pmol/μL). This resulted in a total hybridization volume of 70 μL for each multiplexing case. From this, 20 μL of the hybridization solution for each multiplexing case was deposited over the conjugated barcode spots on the microwell chip and incubated at 40° C. for 20 minutes. The microwell chip was then submerged in 10 mL of washing buffer (0.5×SSC, 0.1% SDS, heated to 40° C.), washed by agitation for 20 s, washed again in another 10 mL of washing buffer to further reduce non-specific binding, and then let dry for 5 minutes before being imaged. Note that care must be taken so that the washing buffer does not dry and crystallize over the sample spots.

Sample Imaging

All images were acquired using the iPhone™ 4S from Apple (unless otherwise specified), mounted on an Olympus IX70 Inverted microscope at 10× magnification for all assays (10× objective, NA=0.30) or 32× magnification for all photographs (20× objective, NA=0.50, with 1.6× further magnification). Quantum dot barcodes and Alexa647 fluorophore were excited using a mercury lamp attached to the microscope, through excitation-emission filter sets [$\lambda$ex=350/50, $\lambda$em=430LP] (Thorlabs), [$\lambda$ex=480/40, $\lambda$em=530/10] (Thorlabs), [$\lambda$ex=480/40, $\lambda$em=580/10] (Thorlabs), [$\lambda$ex=480/40, $\lambda$em=640/10] (Thorlabs), and [$\lambda$ex=620/40, $\lambda$em=692/40] (Semrock, Brightline Cy5-4040A). The emission filters $\lambda$em=530/10, $\lambda$em=580/10, and $\lambda$em=640/10 corresponded with quantum dots QD540, QD589, and QD640, respectively, and were used to isolate for their fluorescence for resolving barcodes. The emission filter $\lambda$em=692/40 was used to isolate for the detection strand Alexa647 fluorophore fluorescence as a means to measure the amount of analyte that hybridized with its corresponding capture strand. Image exposure times, made adjustable with the use of the NightCap app from Apple's App Store, were 1/20, 1/5, 1/5, 1/5, and 1 s for the emission filters $\lambda$em=430LP, $\lambda$em=530/10, $\lambda$em=580/10, $\lambda$em=640/10, and $\lambda$em=692/40, respectively.

Image Analysis

Figure 6:
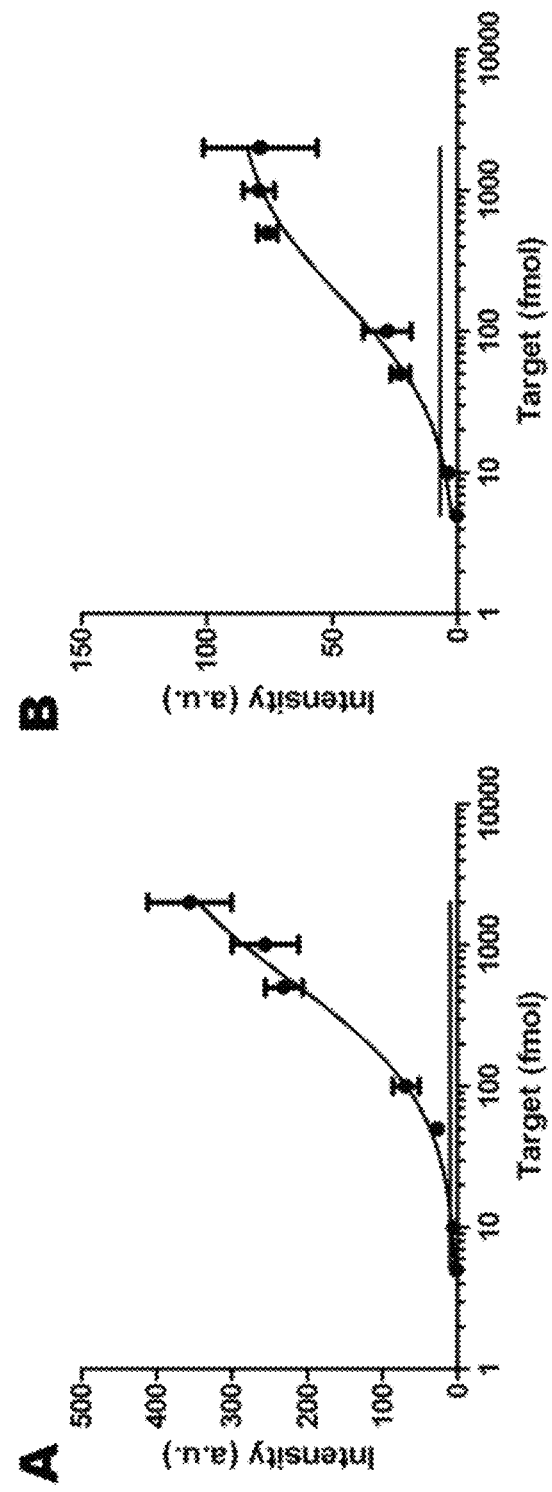
FIG. 6 illustrates a comparison of sensitivity curves obtained from images taken with (A) a charge-coupled device (CCD) camera (Retiga EXi Fast 1394, QImaging) and (B) an iPhone™ camera (iPhone™ 4S, Apple Inc.), for a custom-designed sequence (capture sequence: 5'-GAG ACC ATC AAT GAG GAA GCT GCA GAA TGG GAT-3' (SEQ ID NO: 16); target sequence: 5'-CGG CGA TGA ATA CCT AGC ACA CTT A CTA AT CCC ATT CTG CAG CTT CCT CAT TGA TGG TCT C-3' (SEQ ID NO: 17); secondary probe sequence: 5'-Alexa647-TAA GTG TGC TAG GTA TTC ATC GCC G-3') (SEQ ID NO: 18). The horizontal lines represent the limits of detection and are 15 fmol for both cases. All error bars were calculated based on the standard deviation from three replications.

A custom-made algorithm was written in MathWork's MATLAB for all image analysis. The algorithm accepts as inputs five emission filter images ($\lambda$em=430LP, $\lambda$em=530/10, $\lambda$em=580/10, $\lambda$em=640/10, and $\lambda$em=692/40) that include samples and the same filter images of the microwell chips without beads for background intensity adjustment. The images were cropped to include beads of interest based on user selection. The cropped filter images were aligned with the $\lambda$em=430LP filter image through the use of the Discrete Fourier Transform registration (21, 22). The algorithm then identified the size and location of each bead, based on its appearances in the $\lambda$em=430LP filter image, using the Hough transform (23, 24). Each bead was then associated with the mean pixel intensity across its area at each of the four remaining filter images. For each bead, the $\lambda$em=530/10, $\lambda$em=580/10, and $\lambda$em=640/10 filter image intensities comprised its intensity profile, while the $\lambda$em=692/40 filter image intensity indicated the secondary probe intensity. In order to identify the barcodes on the chip, known barcode intensity profiles were first established (FIG. 6). These profiles were obtained by imaging the barcodes B1 to B7 (see FIG. 8) alone and calculating the median filter intensity across all beads for each filter. A bead's intensity profile was then compared against each known barcode's intensity profile to identify the barcode of interest. Specifically, a barcode was first coarsely classified according to its highest intensity among the filters $\lambda$em=530/10, $\lambda$em=580/10, and $\lambda$em=640/10. Euclidean distances between the bead intensity profile and the known barcode intensity profiles were calculated:

$$D_N = |I - I_{B_N}| = \sqrt{\begin{array}{c}(I_{F_1} - I_{B_N F_1})^2 + (I_{F_2} - I_{B_N F_2})^2 + \\ (I_{F_3} - I_{B_N F_3})^2 + \ldots + (I_{F_M} - I_{B_N F_M})^2\end{array}} \quad [1]$$

$D_N$=Euclidean distance between the bead intensity profile and Barcode N (B1 to B7) intensity profile.

$I_{F_M}$=Intensity of bead at Filter M (λem=530/10, λem=580/10, λem=640/10).

$I_{B_N F_M}$=Intensity of Barcode N (B1 to B7) at Filter M (λem=530/10, λem=580/10, λem=640/10).

The barcode of interest was identified as the barcode whose known intensity profile resulted in the smallest Euclidean distance. Finally, the median assay intensity (i.e. λem=692/40 filter intensity) was calculated for all beads with the same barcode, and defined as that barcode's hybridization signal. Note that the corresponding background intensities were subtracted from 305 the recorded intensities to adjust for possible intensity variations inherent in the chips or excitation source. The secondary probe intensities were further subtracted by their corresponding barcodes' blank signal at the intensities from λem=692/40 filter (black bars of FIG. 5).

Results and Discussion

We evaluated whether the camera from a wireless communications device, in this case a smartphone, is capable of imaging the different fluorescent emitting barcodes, and whether a custom algorithm can be used to differentiate the optical signal from the secondary fluorescent label. We first confirmed that a smartphone camera had the imaging resolution and sensitivity to identify each of the barcoded beads on the chip. We designed five uniquely fluorescent quantum dot barcodes and assembled them on the surface of the chip. These barcodes contained quantum dots emitting at wavelengths of 540, 589, and 640 nm mixed in various ratios (FIG. 8). We placed this chip on the surface of a microscope stage, excited with Hg lamp (λex=350/50), collected the optical signal with an objective (20× at NA=0.50), filtered the emission (λem=430LP), and imaged using an Apple iPhone™ 4S smartphone (exposure time=1/20 s) attached to the eyepiece of the microscope. FIG. 10 clearly shows the ability to visually discriminate the fluorescence emission of the different barcodes.

We then developed an algorithm using MathWorks' MAT-LAB that can identify barcodes and the secondary probe's signal. The algorithm accepted as inputs five emission filter images (λem=430LP, λem=530/10, λem=580/10, λem=640/10, and λem=692/40) that included samples and the same filter images of the microwell chips without beads for background intensity adjustment.

By way of example only, our system consists of an Apple iPhone™ 4S smartphone mounted onto the front port of a microscope and a mercury lamp to excite the barcodes on the chip. The algorithm is designed to identify the barcodes by comparing the optical signal of each microbead in the wells to that of a known panel of barcodes (see FIG. 5). With reference to FIG. 2 A, green 210, yellow 212 and red 214 barcodes (identified as B1, B4, and B6 in FIG. 8 respectively) were deposited on the chip and imaged using an iPhone™. FIG. 2a demonstrates that an iPhone™ camera is able to capture the distinct optical emission of each barcode in the well. After the assay, the smartphone camera-acquired fluorescence image of the microbeads bound with the target analyte and secondary probe (fluorescence microscopy parameters: objective of 20× at NA=0.50, λex=640/40, and λem=692/40, exposure time=1 s). Both green and red beads had positive signals. This demonstrates that T1 and T6 genomic targets are present in the sample but not T4. Of note, the white spots on the barcodes are due to overexposure from the high combined intensity of the Alexa647 fluorophore and the 640 nm quantum dots impregnated within B6. FIG. 2b shows that the barcodes' optical signals can be differentiated from the secondary probe using proper filtering. We next compared the analytical performance of the iPhone™ camera with an expensive charge-coupled device (CCD) camera in detecting target analytes on a chip.

By way of example, using a model genomic sequence, we illustrated the sandwich architecture of the final microbead complex for a positive detection. We prepared a chip containing a single fluorescing barcode that was conjugated with the sequence 5'-GAG ACC ATC AAT GAG GAA GCT GCA GAA TGG GAT-3' (SEQ ID NO: 16). We added a solution containing the target sequence 5'-CGG CGA TGA ATA CCT AGC ACA CTT A CTA AT CCC ATT CTG CAG CTT CCT CAT TGA TGG TCT C-3' (SEQ ID NO: 17) and an Alexa647 dye labeled secondary sequence 5'-Alexa647-TAA GTG TGC TAG GTA TTC ATC GCC G-3' (SEQ ID NO: 18). For a positive detection, the optical signal from the microbead comprises the quantum dots in the barcode and the Alexa dye. The target sequence would hybridize to both the secondary probe and the barcode, and that the fluorescence intensity of the Alexa dye identifies the concentration of the target analyte. We showed that an iPhone™ camera produced a similar limit of detection and dynamic range compared to the expensive CCD camera (see FIG. 6). These studies confirmed that an iPhone™ camera can image barcodes on the chip surface, be used as a detector for biological assays, and can reduce the cost and size of a quantum dot barcode detection system.

The only other study using a phone camera for molecular detection of infectious diseases did not provide analytical curves to evaluate the performance of the lateral flow assay (5). Lateral flow assay also cannot be multiplexed and therefore, this technique is limited to detecting a molecule that is present at thigh concentrations.

While lateral flow systems are preferentially used in developing countries due to their simplicity for detection of disease markers, they typically have an inferior limit of detection in the range of mM to μM, and have limited capacity in analyzing multiple biomarkers simultaneously. A key advantage of quantum dot barcodes is that the different colors and intensity combinations of quantum dots inside the microbeads can produce a large library of barcodes, providing significant multiplexing capabilities. Nie and co-workers estimated that 10,000 to 40,000 different barcodes could be generated using 5 to 6 different emitting quantum dots (14).

By way of example, we selected genetic targets for influenza A viruses H1N1, H3N2, and H5N1, and 20 hepatitis B and C to demonstrate the use of our integrated wireless communications device quantum dot barcode chip system for multiplex detection. The influenza A viruses are airborne, highly contagious, share similar symptoms, have posed significant difficulty in clinical differential diagnosis, and remain pandemic risks (8, 9). The blood-borne viruses hepatitis B (HBV) and hepatitis C (HCV) are prevalent in resource-limited settings (10). These infections are difficult to differentiate clinically since they share common symptoms such as general malaise, jaundice, and nausea and/or vomiting (11).

We designed seven barcodes for each of five infectious disease biomarker targets plus a negative and positive control (see FIG. 8). The analytical sensitivity and linear dynamic range for each of the barcode (see FIG. 2C) is on average 50 fmol and up to 100-fold, respectively. Here we demonstrated that our chip is able to detect multiple biomarker targets simultaneously. We prepared six different mock genetic samples by mixing different combinations of the genetic target sequences for each of the five pathogens of interest plus a positive control sequence, and a secondary fluorescent probe sequence. For example, we would prepare solutions that were spiked with the target sequences T1, T3, T5, and T7, or T2, T4, and T7. A sample of 10 µL was added to the chip and incubated at 40° C. for 20 minutes, rinsed with a washing buffer, dried, imaged, and analyzed using the algorithm. FIG. 3 shows that we can identify all the target biomarkers in solution for all six samples. For example, in FIG. 3B, our solution contained the sequences T1, T3, T5, and T7 and the bar graph shows our technique can discriminate between barcode containing a secondary probe versus those that do not (T2, T4, and T6).

It has been demonstrated herein that the combination of quantum dot barcodes with wireless communications device technologies to engineer a device capable of detecting different types of targets, in this example, infectious diseases markers. There are two major inventive aspects to the present invention: (a) barcodes can now be easily transported on a chip and (b) integration of barcodes with portable wireless communications device technology enables multiplex detection anywhere in the world without the need for skilled technicians to interpret the data. This detection device enables hospitals, environmental control agencies, disease control centers, and the military to monitor the onset and spread of contaminants, pathogens and other targets of interest and it can be used at point-of-care and in care settings to identify targets associated with cancer, diabetes, or cardiovascular diseases, and other diseases or disease markers, as well as other agriculturally and environmentally relevant pathogens and contaminants.

TABLE 1

SEQ. ID NOs

| Code: | SEQ ID NO: | Sequence: |
|---|---|---|
| C1 | SEQ ID NO: 1 | ccc tct tag ttt gca tag ttt ccc gtt atg |
| C2 | SEQ ID NO: 2 | act tgg ttg ttt ggg ggg gag ttg aat tca |
| C3 | SEQ ID NO: 3 | cca ttc cct gcc atc ctc cct cta taa aac |
| C4 | SEQ ID NO: 4 | tca gaa ggc aaa aaa gag agt aac t |
| C5 | SEQ ID NO: 5 | cat agt ggt ctg cgg aac cgg tga gt |
| C6 | SEQ ID NO: 6 | gac aat gct cac tga gga tag t |
| C7 | SEQ ID NO: 7 | cca ata tcg gcg gcc |
| T1 | SEQ ID NO: 8 | cgg cga tga ata cct agc aca ctt a cta ca taa cgg gaa act atg caa act aag agg g |
| T2 | SEQ ID NO: 9 | cgg cga tga ata cct agc aca ctt a cta tg aat tca act ccc ccc caa aca acc aag t |

TABLE 1-continued

SEQ. ID NOs

| Code: | SEQ ID NO: | Sequence: |
|---|---|---|
| T3 | SEQ ID NO: 10 | cgg cga tga ata cct agc aca ctt a cta gt ttt ata gag gga gga tgg cag gga atg g |
| T4 | SEQ ID NO: 11 | cgg cga tga ata cct agc aca ctt a cta ag tta ctc tct ttt ttg cct tct ga |
| T5 | SEQ ID NO: 12 | cgg cga tga ata cct agc aca ctt a cta ac tca ccg gtt ccg cag acc act atg |
| T6 | SEQ ID NO: 13 | cgg cga tga ata cct agc aca ctt a cta ac tat cct cag tga gca ttg tc |
| T7 | SEQ ID NO: 14 | cgg cga tga ata cct agc aca ctt act agg ccg ccg ata ttg g |
| D | SEQ ID NO: 15 | Alexa647-taa gtg tgc tag gta ttc atc gcc g |

TABLE 2

List of microbeads synthesized.

| Barcode | Diameter (µm) | QD540 Concentration (µL/mL) | QD589 Concentration (µL/mL) | QD640 Concentration (µL/mL) |
|---|---|---|---|---|
| B1 | 2.70 ± 1.61 | 60 | | |
| B2 | 2.70 ± 1.36 | | 57 | |
| B3 | 2.70 ± 1.60 | 60 | 11.4 | |
| B4 | 2.70 ± 1.60 | 12 | 57 | |
| B5 | 2.70 ± 1.34 | | 57 | 182 |
| B6 | 3.50 ± 1.19 | | | 910 |
| B7 | 2.70 ± 1.51 | | | 182 |

REFERENCES

1. Yager P et al. (2006) Microfluidic diagnostic technologies for global public health. Nature 442:412-8. 335
2. Chin C D, Linder V, Sia S K (2007) Lab-on-a-chip devices for global health: past studies and future opportunities. Lab on a chip 7:41-57.
3. Martinez A W, Phillips S T, Whitesides G M, Carrilho E (2010) Diagnostics for the developing world: microfluidic paper-based analytical devices.
4. International Telecommunication Union Statistics Available at: 340 http://www.itu.int/ict/statistics.
5. Mudanyali O et al. (2012) Integrated rapid-diagnostic-test reader platform on a cellphone. Lab Chip. 2012 Aug. 7; 12(15):2678-86.
6. Zhu H, Sikora U, Ozcan A (2012) Quantum dot enabled detection of *Escherichia coli* using a cell-phone. The Analyst 137:2541-4. 345
7. Breslauer D N, Maamari R N, Switz N a, Lam W a, Fletcher D a (2009) Mobile phone based clinical microscopy for global health applications. PloS One 4:e6320.
8. Korteweg C, Gu J (2010) Pandemic influenza A (H1N1) virus infection and avian influenza A (H5N1) virus infection: a comparative analysis. Biochemistry and Cell Biology=Biochimie et Biologie Cellulaire 88:575-87. 350

9. Smith G J D et al. (2009) Dating the emergence of pandemic influenza viruses. Proceedings of the National Academy of Sciences of the United States of America 106:11709-12.
10. Yerly S et al. (2001) Nosocomial outbreak of multiple bloodborne viral infections. The Journal of Infectious Diseases 184:369-72.
11. Chu C et al. (2001) Hepatitis C: Comparison with acute heptitis B—Comparison of clinical, 355 virologic and pathologic features in patients with acute hepatitis B and C. Journal of Gastroenterology and Hepatology 16:209-214.
12. Girl S, Sykes E A, Jennings T L, Chan W C W (2011) Rapid screening of genetic biomarkers of infectious agents using quantum dot barcodes. ACS Nano 5:1580-7.
13. Klostranec J M et al. (2007) Convergence of quantum dot barcodes with microfluidics and 360 signal processing for multiplexed high-throughput infectious disease diagnostics. Nano Letters 7:2812-8.
14. Han M, Gao X, Su J Z, Nie S (2001) Quantum-dot-tagged microbeads for multiplexed optical coding of biomolecules. Nature Biotechnology 19:631-5.
15. Walt D R (2010) Fibre optic microarrays. Chemical Society Reviews 39:38-50. 365
16. Zhu H, Mavandadi S, Coskun A F, Yaglidere O, Ozcan A (2011) Optofluidic fluorescent imaging cytometry on a cell phone. Analytical chemistry 83:6641-7.
17. Fournier-Bidoz S et al. (2008) Facile and rapid one-step mass preparation of quantum-dot barcodes. Angewandte Chemie (International ed in English) 47:5577-81.
18. Peng X, Schlamp M C, Kadavanich A V, Alivisatos A P (1997) Epitaxial Growth of Highly 370 Luminescent CdSe/CdS Core/Shell Nanocrystals with Photostability and Electronic Accessibility. Journal of American Chemical Society 119:7019-7029.
19. Hines M A, Guyot-Sionnest P (1996) Synthesis and Characterization of Strongly Luminescing ZnS-Capped CdSe Nanocrystals. The Journal of Physical Chemistry 100:468-471. 375
20. Dabbousi B O et al. (1997) (CdSe) ZnS Core-Shell Quantum Dots: Synthesis and Characterization of a Size Series of Highly Luminescent Nanocrystallites. Journal of Physical Chemistry B 101:9463-9475.
21. Guizar-Sicairos M, Thurman S T, Fienup J R (2008) Efficient subpixel image registration algorithms. Optics Letters 33:156-8. 380
22. Guizar-Sicairos M Efficient subpixel image registration by cross-correlation. Available at: http://www.mathworks.com/matlabcentral/fileexchange/18401-efficient-subpixel-image-registration-by-cross-correlation.
23. Ballard D H (1981) Generalizing the Hough Transform to detect arbitrary shapes. Pattern Recognition 13:111-122.385
24. Peng T Detect circles with various radii in grayscale image via Hough Transform. Available at: http://www.mathworks.com/matlabcentral/fileexchange/9168-detect-circles-with-various-radii-in-grayscale-image-via-hough-transform.

Through the embodiments that are illustrated and described, the currently contemplated best mode of making and using the invention is described.

Without further elaboration, it is believed that one of ordinary skill in the art can, based on the description presented herein, utilize the present invention to the full extent. All publications cited herein, as well as the priority document, are incorporated by reference in their entirety.

Therefore what is claimed is:

1. A portable detection system for simultaneous identification of multiple targets of interest, the system comprising:
   (a) a portable multiplex detector comprising (i) a substrate placed on the surface of a stage, and (ii) a plurality of pairs of primary labels and a secondary labels for each of the multiple targets of interest, the primary and secondary labels being coupled to a surface of the substrate, each primary label being bound to a first ligand specific to one of the targets of interest, each primary label being capable of emitting a first signal corresponding to the target-specific first ligand when exposed to an excitation source, and the secondary label being bound either the first ligand or to a second ligand specific to the same target of interest as the first ligand and the secondary label being capable of emitting a second signal when exposed to the excitation source, the combination of the first and second signals of one population producing an overall signal in the presence of a target of interest, the primary label comprises fluorescent quantum dot barcodes in the visual spectrum and the secondary label comprises fluorophores;
   (b) an objective lens for collecting emissions from the substrate;
   (c) a filter for filtering the emissions from the substrate;
   (d) an eyepiece for collecting the filtered emissions;
   (e) a portable wireless communication device attached to the eyepiece for receiving the filtered emissions and imaging such emissions, wherein the portable wireless communication device is programmed with algorithms for comparing the barcodes and signals from the labels to a known panel of barcodes and signals for the targets of interest and for identifying the barcodes and signals from the labels based on said comparison, the portable wireless communication device being a device using radio-frequency, infrared, microwave, or other types of electromagnetic or acoustic waves in place of wires, cables, or fibre optics to transmit or receive signals or data, and the portable wireless communication device including a camera for acquiring images, signals or data and processors for analyzing the images, signals or data, the portable wireless communication device being a portable computer; and
   (f) the excitation source, wherein the excitation source is directed at the substrate for exciting the labels.

2. The system of claim 1, wherein the ligands include nucleotide-based ligands, amino acid-based ligands, polysaccharide-based ligands, protein based ligands, antigens, antibodies, and hormones, or other organic or inorganic molecules.

3. The system of claim 1, wherein each of the barcodes include 5 to 6 different emitting quantum dots.

4. The system of claim 1, wherein the substrate is a static substrate having a substantially flat surface, and wherein the substrate is selected from the group consisting of glass, paper, cellulose or plastic.

5. The system of claim 1, wherein the substrate is a dynamic substrate, the dynamic substrate comprising micro channels or capillary networks.

6. The system of claim 1, wherein the surface of the substrate comprises a plurality of indentations capable of receiving the populations of primary and secondary labels.

7. The system of claim 1, wherein the algorithms includes instructions for quantification of the multiple targets.

8. The system of claim 1, wherein the ligand include ligand to unicellular and multicellular microorganisms, inorganic molecules and organic molecules.

9. The system of claim 8, wherein the organic molecules include peptides, proteins, oligosaccharides, lipids, genes, nucleic acid sequences, amino acid sequences, RNA sequences and DNA sequences and wherein inorganic molecules contain metal atoms.

10. A method for simultaneously identifying the presence of multiple targets of interest in a sample, the method comprising: (a) providing the system of claim 1, (b) contacting the sample with the portable multiplex detector; (c) collecting the signals via the portable wireless communication device; and (d) analyzing the collected signals using the portable wireless communication device by comparing the collected signals with the known panel of barcodes and signals for the targets of interest to identify the presence of the multiple targets of interest in the sample, whereby the presence of one target in the sample is identified when the overall signal corresponding to said one target is collected.

11. A portable detection system for simultaneous identification of multiple targets of interest, the system comprising:
  (a) a portable multiplex detector comprising (i) a substrate placed on the surface of a stage, and (ii) a plurality of pairs of primary labels and a secondary labels for each of the multiple targets of interest, the primary and secondary labels being coupled to a surface of the substrate, each primary label being bound to a first ligand specific to one of the targets of interest, each primary label being capable of emitting a first signal corresponding to the target-specific first ligand when exposed to an excitation source, and the secondary label being bound either the first ligand or to a second ligand specific to the same target of interest as the first ligand and the secondary label being capable of emitting a second signal when exposed to the excitation source, the combination of the first and second signals of one population producing an overall signal in the presence of a target of interest, the primary label comprises fluorescent quantum dot barcodes in the visual spectrum and the secondary label comprises fluorophores;
  (b) an objective lens for collecting emissions from the substrate;
  (c) a filter for filtering the emissions from the substrate;
  (d) an eyepiece for collecting the filtered emissions;
  (e) a portable wireless communication device attached to the eyepiece for receiving the filtered emissions and imaging such emissions, wherein the portable wireless communication device is programmed with algorithms for comparing the barcodes and signals from the labels to a known panel of barcodes and signals for the targets of interest and for identifying the barcodes and signals from the labels based on said comparison, the portable wireless communication device being a device using radio-frequency, infrared, microwave, or other types of electromagnetic or acoustic waves in place of wires, cables, or fibre optics to transmit or receive signals or data, and the portable wireless communication device including a camera for acquiring images, signals or data and processors for analyzing the images, signals or data, the portable wireless communication device being selected from the group consisting of: a smart phone and a personal assistant device; and
  (f) the excitation source, wherein the excitation source is directed at the substrate for exciting the labels.

12. The system of claim 11, wherein the ligands include nucleotide-based ligands, amino acid-based ligands, polysaccharide-based ligands, protein based ligands, antigens, antibodies, and hormones, or other organic or inorganic molecules.

13. The system of claim 11, wherein each of the barcodes include 5 to 6 different emitting quantum dots.

14. The system of claim 11, wherein the substrate is a static substrate having a substantially flat surface, and wherein the substrate is selected from the group consisting of glass, paper, cellulose or plastic.

15. The system of claim 11, wherein the substrate is a dynamic substrate, the dynamic substrate comprising micro channels or capillary networks.

16. The system of claim 11, wherein the surface of the substrate comprises a plurality of indentations capable of receiving the populations of primary and secondary labels.

17. The system of claim 11, wherein the algorithms includes instructions for quantification of the multiple targets.

18. The system of claim 11, wherein the ligand include ligand to unicellular and multicellular microorganisms, inorganic molecules and organic molecules.

19. The system of claim 18, wherein the organic molecules include peptides, proteins, oligosaccharides, lipids, genes, nucleic acid sequences, amino acid sequences, RNA sequences and DNA sequences and wherein inorganic molecules contain metal atoms.

20. A method for simultaneously identifying the presence of multiple targets of interest in a sample, the method comprising: (a) providing the system of claim 11, (b) contacting the sample with the portable multiplex detector; (c) collecting the signals via the portable wireless communication device; and (d) analyzing the collected signals using the portable wireless communication device by comparing the collected signals with the known panel of barcodes and signals for the targets of interest to identify the presence of the multiple targets of interest in the sample, whereby the presence of one target in the sample is identified when the overall signal corresponding to said one target is collected.

* * * * *

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
ccctcttagt ttgcatagtt tcccgttatg                                    30

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
acttggttgt ttgggggga gttgaattca                                     30

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
ccattccctg ccatcctccc tctataaaac                                    30
```

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
tcagaaggca aaaagagag taact                                         25

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
catagtggtc tgcggaaccg gtgagt                                       26

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gacaatgctc actgaggata gt                                           22

<210> SEQ ID NO 7
<211> LENGTH: 15
<212> TYPE: DNA
<213> ORGANISM: Artificial Sequence
<220> FEATURE:
<223> OTHER INFORMATION: Synthetic

<400> SEQUENCE: 7
ccaatatcgg cggcc                                                   15

<210> SEQ ID NO 8
<211> LENGTH: 58
<212> TYPE: DNA
<213> ORGANISM: Artificial Sequence
<220> FEATURE:
<223> OTHER INFORMATION: Synthetic

<400> SEQUENCE: 8
cggcgatgaa tacctagcac acttactaca taacgggaaa ctatgcaaac taagaggg    58

<210> SEQ ID NO 9
<211> LENGTH: 58
<212> TYPE: DNA
<213> ORGANISM: Artificial Sequence
<220> FEATURE:
<223> OTHER INFORMATION: Synthetic

<400> SEQUENCE: 9
cggcgatgaa tacctagcac acttactatg aattcaactc cccccaaac aaccaagt     58

<210> SEQ ID NO 10
<211> LENGTH: 58
<212> TYPE: DNA
<213> ORGANISM: Artificial Sequence
<220> FEATURE:

```
<223> OTHER INFORMATION: Synthetic

<400> SEQUENCE: 10
cggcgatgaa tacctagcac acttactagt tttatagagg gaggatggca gggaatgg      58

<210> SEQ ID NO 11
<211> LENGTH: 53
<212> TYPE: DNA
<213> ORGANISM: Artificial Sequence
<220> FEATURE:
<223> OTHER INFORMATION: Synthetic

<400> SEQUENCE: 11
cggcgatgaa tacctagcac acttactaag ttactctctt ttttgccttc tga           53

<210> SEQ ID NO 12
<211> LENGTH: 54
<212> TYPE: DNA
<213> ORGANISM: Artificial Sequence
<220> FEATURE:
<223> OTHER INFORMATION: Synthetic

<400> SEQUENCE: 12
cggcgatgaa tacctagcac acttactaac tcaccggttc cgcagaccac tatg          54

<210> SEQ ID NO 13
<211> LENGTH: 50
<212> TYPE: DNA
<213> ORGANISM: Artificial Sequence
<220> FEATURE:
<223> OTHER INFORMATION: Synthetic

<400> SEQUENCE: 13
cggcgatgaa tacctagcac acttactaac tatcctcagt gagcattgtc               50

<210> SEQ ID NO 14
<211> LENGTH: 43
<212> TYPE: DNA
<213> ORGANISM: Artificial Sequence
<220> FEATURE:
<223> OTHER INFORMATION: Synthetic

<400> SEQUENCE: 14
cggcgatgaa tacctagcac acttactagg ccgccgatat tgg                      43

<210> SEQ ID NO 15
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Alexa647 dye label

<400> SEQUENCE: 15
taagtgtgct aggtattcat cgccg                                          25

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
```

```
gagaccatca atgaggaagc tgcagaatgg gat                                    33

<210> SEQ ID NO 17
<211> LENGTH: 61
<212> TYPE: DNA
<213> ORGANISM: Artificial Sequence
<220> FEATURE:
<223> OTHER INFORMATION: Synthetic

<400> SEQUENCE: 17
cggcgatgaa tacctagcac acttactaat cccattctgc agcttcctca ttgatggtct      60
c                                                                       61

<210> SEQ ID NO 18
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Alexa647 dye label

<400> SEQUENCE: 18
taagtgtgct aggtattcat cgccg                                             25
```